United States Patent [19]

Seidelmann et al.

[11] 4,080,456
[45] Mar. 21, 1978

[54] DIACYLAPOMORPHINES

[75] Inventors: Dieter Seidelmann; Ralph Schmiechen; Reinhard Horowski; Wolfgang Kehr; Dieter Palenschat; Gert Paschelke, all of Berlin, Germany

[73] Assignee: Schering Aktiengesellschaft, Berlin and Bergkamen, Germany

[21] Appl. No.: 633,650

[22] Filed: Nov. 20, 1975

Related U.S. Application Data

[63] Continuation of Ser. No. 301,153, Oct. 26, 1972, abandoned.

[30] Foreign Application Priority Data

Oct. 26, 1971 Germany ............... 2154162

[51] Int. Cl.² .............. A61K 31/47; C07D 215/06
[52] U.S. Cl. ............................. 424/258; 260/287 P
[58] Field of Search ............. 260/287 P, 285; 424/258

[56] References Cited

U.S. PATENT DOCUMENTS 3,717,639 2/1973 Neumeyer ............... 260/285
3,717,643 2/1973 Archer ................... 260/285

OTHER PUBLICATIONS

Lecomte et al., "Chemical Abstracts," vol. 58, 6104d, (1962).
Ibid. Janssen et al., vol. 55, 8659f, (1960).
Cannon et al., "J. Pharm. Sci.," 52, (11), 1112–1113, (1963).
Dictionary of Organic Compounds, Oxford Press (1965).

*Primary Examiner*—R. Gallagher
*Assistant Examiner*—David E. Wheeler
*Attorney, Agent, or Firm*—Millen & White

[57] ABSTRACT

Diacylapomorphines of the formula

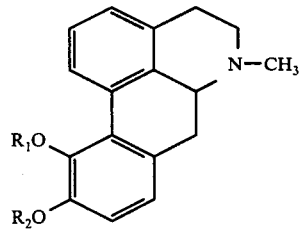

wherein $R_1$ and $R_2$ are both acyl of 1–17 carbons are symptomatically effective agents in the treatment of motor disorders of the type associated with a dopamine deficiency of the extrapyramidal system of the central nervous system, e.g. Parkinson's disease. Pharmaceutical compositions containing these compounds as an active ingredient are described, as well as new compounds of the above formula wherein $R_1$ and $R_2$ are formyl or acyl of 3–17 carbon atoms.

13 Claims, No Drawings

DIACYLAPOMORPHINES

This is a continuation of application Ser. No. 301,153 filed Oct. 26, 1972 now abandoned.

BACKGROUND OF THE INVENTION

This invention relates to diacylapomorphines, drugs containing diacylapomorphines, and process for the use of diacylapomorphines.

It is known that the primary motor disorder symptoms of "morbus Parkinson," such as tremor, rigor, and akinesia, are favorably affected by apomorphine (Ann. Rep. of Med. Chem. 1970, P. 42). However, many inherent disadvantages are encountered when using apomorphine, e.g., a short duration of action, a relatively high toxicity, and the ready oxidation of apomorphine into toxic oxidation products. It is believed that apomorphine oxidation products may lead to complications, e.g., cardiovascular collapse has been noted after the injection of apomorphine solutions which are slightly colored due to oxidation.

OBJECTS OF THE INVENTION

Accordingly, it is an object of this invention to provide new and useful derivatives of apomorphine.

Another object of this invention is to provide a pharmaceutical composition containing one or more apomorphine derivatives as a therapeutically effective active ingredient suitable for the treatment of the symptoms of paralysis agitans or Parkinson's disease.

A further object of this invention is to provide a process for the alleviation of motor disorders associated with paralysis agitans.

A more particular object of the present invention is to provide compounds which exhibit, together with an effectiveness against the symptoms of paralysis agitans comparable to apomorphine, a longer duration of action and significantly lower toxicity.

Upon further study of the specification and appended claims, further objects and advantages of this invention will become apparent to those skilled in the art.

SUMMARY OF THE INVENTION

The above and other objects are attained in a pharmaceutical composition aspect of this invention by providing a pharmaceutical composition suitable for the treatment of motor disorders of the type associated with paralysis agitanus which comprises a tremor-reducing effective amount of a compound according to Formula I:

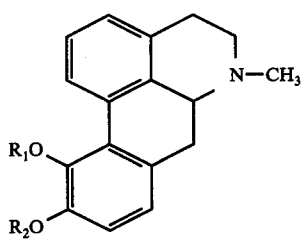

I wherein $R_1$ and $R_2$ are both acyl of 1-17 carbon atoms, or the physiologically acceptable acid addition salts thereof, together with a major amount of a pharmaceutically acceptable carrier.

In a process aspect, the present invention provides a process for the alleviation of motor disorders of the type associated with dopamine deficiency which comprises administering acatalepsy-abolishing effective amount of at least one compound of Formula I to a living animal afflicted with a dopamine deficiency of the extrapyramidal system of its central nervous system (CNS).

In a more particular process aspect, the present invention provides a process for relieving the primary symptoms of Parkinson's disease which comprises administering a symptomatically effective amount of a compound according to Formula I to a living human being afflicted with Parkinson's disease.

In its chemical compound aspect, the present invention provides pharmaceutically useful compounds according to Formula I wherein $R_1$ and $R_2$ are both formyl or acyl of 3-17 carbon atoms.

DETAILED DISCUSSION

It has now been discovered that diacylapomorphine derivatives of up to 17 carbon atoms in the acyl residue, and the physiologically acceptable acid addition salts thereof, possess the desired properties of symptomatic effectiveness, extended duration of effectiveness, and low toxicity when utilized for the treatment of the symptoms of Parkinson's disease. Diacetylapomorphine has been described in J. Org. Chem. 5:384 (1940), but the biological properties of this compound have not as yet been investigated.

Accordingly, this invention relates to the use of diacyl apormorphine derivatives of the formula

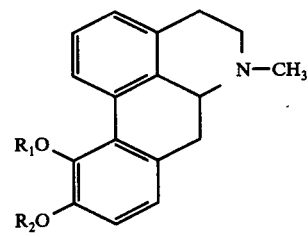

wherein $R_1$ and $R_2$ are both acyl of 1-17 carbon atoms, and the acid addition salts thereof with physiologically compatible acids in the treatment of muscular disorders of the type associated with dopamine insufficiency in extrapyramidal nerve tract centers.

Preferably, $R_1 = R_2$ in the above formula; although there is no apparent reason why they need be identical for purposes of the present invention, compounds in which $R_1$ and $R_2$ are different acyl groups are difficult to prepare and it is more difficult to accurately characterize the effect of a given acyl substituent on the apomorphine molecule.

The term acyl as used herein refers to an organic acid radical of 1-17 carbon atoms customarily employed in esterification reactions and derived from an organic acid by the removal of an acid hydroxyl group, preferably those acid radicals derived from an aliphatic, cycloaliphatic, aryl or heterocyclic aromatic carboxylic or sulfonic acid. Preferred acids are organic carboxylic acids of 1-17 carbon atoms, especially of 3-12 carbon atoms.

It will be apparent to those skilled in the art that the exact nature of the acyl group in $R_1$ and $R_2$ is not critical to the finite utility of the compounds of Formula I in accordance with this invention. Although the acyl group of alkanoic, especially lower alkanoic, i.e., of 1-12 carbon atoms is preferred, a wide variety of acyl groups can be present in the materials of this invention. Thus, equivalents of the compounds of this invention containing at least one acyl group of an alkanoic acid are those wherein the second acyl radical is that of another or preferably the same organic acid, e.g., a carboxylic acid containing up to 17 carbon atoms, especially lower (1-6 carbon atoms) and intermediate (7-12 carbon atoms) aliphatic carboxylic, preferably an alkanoic acid, which can be saturated or olefinically unsaturated, straight or branched. Preferred alkanoic acids include but are not limited to formic, acetic, propionic, butyric, isobutyric, trimethylacetic, α-ethylbutyric, valeric, isovaleric, α-ethylvaleric, 2-methylbutyric, 3-ethylbutyric, hexanoic, diethylacetic, triethylacetic, caproic, enanthic, octanoic, undecyclic, oleic and palmitic acid. Examples of equivalents of such acids are cyclic acids, preferably a cycloaliphatic acid, containing, preferably 4-17 carbon atoms, e.g., cyclopropylacetic, cyclobutylcarboxylic, cyclopentylcarboxylic, cyclopentylacetic, cyclopentylpropionic, cyclohexylacetic and β-cyclohexylpropionic acid; a carbocyclic aryl or alkaryl acid containing 6-17 carbon atoms, and 1 or 2, preferably 1 aromatic ring, e.g., benzoic, 2-, 3-, or 4-methyl-benzoic, 2,3-, 2,4-, 2,5-, 2,6-, 3,4-, and 3,5-dimethylbenzoic, ethylbenzoic, 2,3,6-trimethylbenzoic, and 3-methyl-α-naphthoic acid; an aralkyl acid containing 7 to 17 carbon atoms, e.g., phenylacetic, β-phenylpropionic; a polybasic acid containing 2-17 carbon atoms and 0 to 5 hydroxy groups, e.g., glycolic, lactic, succinic, adipic, citric, tartaric, d-maleic, d-glyceric, and salicyclic acid; the corresponding acids containing one, two or more halo, hydroxy, mercapto, oxo, amino, alkylamino, alkoxy, acyloxy, etc. substituents in the molecule, e.g., mono-, di- and trichloroacetic, fluoroacetic, trichloroacetic, trifluoroacetic, 2,3,4-trimethoxybenzoic, phenoxyacetic, α-naphthoxyacetic acid, nicotinic acid, aminoacetic acid; lower-alkylamino and di-lower-alkylaminoacetic acids, e.g., ethylaminoacetic and diethylaminoacetic; O-, N- or S-heterocyclic substituted-alkanoic acids, e.g., piperidinoacetic and morpholinoacetic acid.

The residues of organic carboxylic acids of 3-17 carbon atoms are preferred. The acids can be saturated, unsaturated, straight-chain, branched, mono- or polybasic, and also substituted on the carbon backbone in the usual manner. Suitable substituents include but are not limited to hydroxy, alkoxy, amino, alkylamino, mercapto, substituted mercapto groups and halogen. Suitable are aliphatic, cycloaliphatic, aromatic, mixed aromatic-aliphatic, and heterocyclic acids, all of which can be substituted in the customary manner.

Especially preferred acids include but are not limited to propionic acid, butyric acid, isobutyric acid, valeric acid, caproic acid, enanthic acid, hexadecanoic acid, pivalic acid, dichloroacetic acid, cyclopentylpropionic acid, phenylacetic acid, diphenylacetic acid, phenylpropionic acid, phenoxyacetic acid, dialkylaminoacetic acid, piperidinoacetic acid, succinic acid, benzoic acid, 3,4-dimethoxy-benzoic acid, 3,4,5-trimethoxybenzoic acid, 4-chlorobenzoic acid, pyridine-3-carboxylic acid, pyridine-4-carboxylic acid, thiophene-2-carboxylic acid, cyclobutane-, cyclopentane-, and cyclohexanecarboxylic acids, adamantanecarboxylic acid, alkoxyacetic acid, dialkylaminobenzoic acid, etc.

Physiologically compatible acids which are suitable for salt formation include but are not limited to hydrochloric acid, sulfuric acid, phosphoric acid, acetic acid, propionic acid, lactic acid, succinic acid, tartaric acid, citric acid, heptagluconic acid, etc. Preferred acids are hydrochloric acid and tartaric acid.

Novel effective agents of the above are those in which $R_1$ and $R_2$ are both formyl or acyl of 3-17 carbon atoms. They can be produced by esterification of apomorphine and optional conversion of the resultant ester into a pharmaceutically acceptable acid addition salt.

The esterification can be effected by conventional methods. Suitable esterification methods include but are not limited to the reaction of apomorphine with acid anhydrides in the presence of a weak base; the Schotten-Baumann reaction; or the reaction with the desired acid in the presence of trifluoroacetic acid anhydride.

Preferred new apomorphine acyl esters of this invention are those compounds which meet one or more of the following criteria:

a. $R_1$ and $R_2$ are identical;
b. $R_1$ and $R_2$ are both formyl;
c. $R_1$ and $R_2$ are both alkanoyl of 3-17 carbon atoms, especially of 3-12 carbon atoms, e.g., propionyl, n-butyryl, caproyl, capryl, hexadecanoyl, etc.;
d. $R_1$ and $R_2$ are both branched chain alkanoyl of 3-17 carbon atoms, especially of 4-8 carbon atoms, e.g., isobutyryl, pivalyl, i-valeryl, etc.;
e. $R_1$ and $R_2$ are both aroyl or substituted aroyl, e.g., phenoxy; benzoyl; alkoxybenzoyl, preferably lower alkoxy of 1-3 carbon atoms and especially methoxy; halophenoxy or halobenzoyl, i.e., substituted with at least one of fluoro, chloro, bromo or iodo, preferably by 1-3 halogen atoms and especially chloro; e.g., phenylacetyl, di- or tri-methoxybenzoyl, chlorobenzoyl, etc.;
f. $R_1$ and $R_2$ are both cycloalkanoyl of 4-12 carbon atoms, e.g., cyclopropanoyl, cyclobutanoyl, cyclopentanoyl, cyclohexanoyl, etc.;
g. $R_1$ and $R_2$ are both acyl radicals of a heterocyclic aromatic acid, preferably wherein heterocyclic is a 5 or 6 member heterocyclic ring having 1-3, preferably one hetero atom, i.e., N, S or O, e.g., pyridoyl, theonyl, etc.
h. $R_1$ and $R_2$ are both the substituted alkanoyl of 3-8 carbon atoms, e.g., methoxyacetyl, phenylacetyl, etc.

Due to their central nervous system activity, the compounds of this invention are useful as tremor-reducing agents in human and verterinary medicine. These compounds are symptomatically effective in the treatment of motor disorders of the type associated with paralysis agitans, and can be used for the reduction of motor disorders of the type associated with dopamine deficiency by administering a catalepsy-abolishing effective amount of a compound according to Formula I to a living animal afflicted with dopamine deficiency of the extrapyramidal system of its CNS. The pharmaceutical compositions of this invention can be employed in substantially the same manner as the known compound apomorphine, but their use in this connection is characterized by a relatively longer duration of action and significantly lower toxicity.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

Suitable for oral administration are, in particular, tablets, dragees, capsules, pills, solutions, and suspensions. Tablets contain, for example, 5–500 mg., preferably 20–200 mg. of effective agent and 50–1000 mg., preferably 50–500 mg. of a pharmacologically indifferent excipient. Suitable excipients for tablets are, for example: lactose, saccharose, sorbitol, mannitol, amyloses, such as potato starch, corn starch, or amylopectin, gelatin, or polyvinylpyrrolidone, optionally with the addition of lubricants, such as magnesium stearate or polyethylene glycols. Dragee cores are thereupon coated with sugar solutions, for example, which can additionally contain gum arabic, talc and/or titanium dioxide.

For parenteral application, particularly suitable are solutions, preferably oily or aqueous solutions, as well as suspensions, emulsions, or implants, including suppositories. Ampoules are convenient unit dosages.

Generally, the compounds of this invention are dispensed in form comprising 1–5000 mg. of a pharmaceutical carrier per each unit dosage, and the amount of active agent of this invention per unit dosage is about 0.5 to 200 mg.

The compounds of this invention are generally administered to animals, including but not limited to mammals, e.g., humans, household pets, laboratory animals, livestock, etc. A tremor-reducing effective daily dosage of the active compounds as administered orally to humans generally comprises about 0.1 to 100, preferably 1 to 10 mg/kg of body weight. The dose can be administered singly or as divided dosages throughout the day.

Oral administration is preferred, the compounds of this invention being particularly valuable in the symptomatic treatment of humans afflicted with Parkinson's disease. In this regard, they can be employed in substantially the same manner as the known compound apomorphine.

It will be appreciated that the actual preferred amounts of active compounds used will vary according to the specific compound being utilized, the particular compositions formulated, the mode of application, and the particular situs and organism being treated. Optimal application rates for a given set of conditions can be ascertained by those skilled in the art using conventional dosage determination tests in view of the above guidelines.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error.

EXAMPLE 1

Dipropionylapomorphine

Under agitation, 4.63 g. (50 millimols) of propionic acid anhydride is added dropwise to a suspension of 4.5 g. (15 millimols) of apomorphine hydrochloride in 10 ml. of pyridine distilled over KOH. The reaction mixture is stirred under a nitrogen atmosphere at 100° C. for 2.5 hours.

After the reaction is terminated, the mixture is poured on about 100 ml. of ice water and acidified with HCl to a pH of 3–4. Then, the mixture is extracted several times with chloroform. The combined organic phases are washed with a saturated sodium bicarbonate solution and a saturated sodium chloride solution, dried over $CaSO_4$, and the solvent removed under vacuum. The crude product is chromatographed over silica gel with benzene/acetone. (2/1)

Yield: 96.6% of theory; m.p. 114°–115° C.

$[\alpha]_D^{23} = -81.2°$ ($CHCl_3$, $c = 0.574$).

EXAMPLE 2

Di-n-butyrylapomorphine 6.08 g. (20 mmol) of apomorphine hydrochloride is suspended in 25 ml. of pyridine distilled over KOH. Under agitation and ice cooling, 6.2 ml. (60 mmol) of n-butyryl chloride is added dropwise to the suspension. The reaction mixture is then heated under a nitrogen atmosphere for 1 hour at 100° C. and worked up as described in Example 1.

Yield: 96% of theory; m.p. 100°–102° C.

$[\alpha]_D^{23} = -76.6°$ ($CHCl_3$, $c = 0.630$).

EXAMPLE 3

Diisobutyrylapomorphine

In accordance with the procedure of Example 2, the above-mentioned compound is obtained from 6.08 g. (20 mmol) of apomorphine hydrochloride and 6.3 ml. (60 mmol) of isobutyryl chloride.

Yield: 62.3% of theory; m.p. 106–107° C.

$[\alpha]_D^{23} = -88.0°$ ($CHCl_3$, $c = 0.622$).

EXAMPLE 4

Dipivaloylapomorphine

According to the process of Example 2, the above-identified compound is produced from 3.04 g. (10 mmol) of apomorphine hydrochloride and 3.96 ml. (30 mmol) of pivaloyl chloride.

Yield: 51.6% of theory.

$[\alpha]_D^{25} = -84.6°$ ($CHCl_3$, $c = 0.646$).

EXAMPLE 5

Divaleroylapomorphine

According to the procedure of Example 1, the aforementioned compound is obtained from 6.08 g. (20 mmol) of apomorphine hydrochloride and 8.8 ml. (44 mmol) of valeric acid anhydride.

Yield: 71.2% of theory.

$[\alpha]_D^{23} = -59.2°$ ($CHCl_3$, $c = 0.656$).

EXAMPLE 6

Di-n-caproylapomorphine

In accordance with the mode of operation of Example 1, the above-identified compound is produced from 3.04 g. (10 mmol) of apomorphine hydrochloride and 5.78 ml. (25 mmol) of n-caproic acid anhydride.

Yield: 83.5% of theory.

$[\alpha]_D^{23.5} = -37.8°$ ($CHCl_3$, $c = 0.590$).

EXAMPLE 7

Dihexadecanoylapomorphine

According to the process of Example 2, the aforementioned compound is obtained from 3.04 g. (10 mmol) of apomorphine hydrochloride and 2.6 ml. (25 mmol) of hexadecanoyl chloride.

Yield: 36% of theory; m.p. 70°–72.5° C.
$[\alpha]_D^{25} = -4.7°$ (CHCl$_3$, c = 0.212).

By the introduction of hydrogen chloride gas into the solution of dihexadecanoylapomorphine in diethyl ether/ethanol, the hydrochloride is produced, m.p. 156°–157° C.

EXAMPLE 8

Dibenzoylapomorphine

According to the procedure of Example 2, the above-mentioned compound is produced from 4.55 g. (15 mmol) of apomorphine hydrochloride and 5.19 ml. (45 mmol) of benzoyl chloride.

Yield: 52.6% of theory; m.p. 153°–154° C.
$[\alpha]_D^{23} = +50.3°$ (CHCl$_3$, c = 0.654).

EXAMPLE 9

Diphenylacetylapomorphine

In accordance with the procedure described in Example 1, the above-identified compound is obtained from 4.55 g. (15 mmol) of apomorphine hydrochloride and 5.95 ml. (45 mmol) of phenylacetyl chloride.

Yield: 50% of theory.
$[\alpha]_D^{23} = -47.6°$ (CHCl$_3$, c = 0.660).

EXAMPLE 10

Bis(3,4-dimethoxybenzoyl)apomorphine

In accordance with the process of Example 2, the above-mentioned compound is produced from 4.55 g. (15 mmol) of apomorphine hydrochloride and 10.0 g. (50 mmol) of 3,4-dimethoxybenzoyl chloride.

Yield: 89.4% of theory; m.p. 99°–101° C.
$[\alpha]_D^{23} = +60°$ (CHCl$_3$, c = 0.604).

EXAMPLE 11

Bis(3,4,5-trimethoxybenzoyl)apomorphine

In accordance with the mode of operation of Example 2, the aforementioned compound is obtained from 4.55 g. (15 mmol) of apomorphine hydrochloride and 10.4 g. (45 mmol) of 3,4,5-trimethoxybenzoyl chloride.

Yield: 18.1% of theory; m.p. 186°–188.5° C.
$[\alpha]_D^{24} = +41.5°$ (CHCl$_3$, c = 0.518).

EXAMPLE 12

Di-4-chlorobenzoylapomorphine

According to the process of Example 2, the above-identified compound is produced from 4.55 g. (15 mmol) of apomorphine hydrochloride and 7.88 g. (45 mmol) of 4-chlorobenzoyl chloride.

Yield: 99.5% of theory; m.p. 182°–184° C.
$[\alpha]_D^{23} = +76.5°$ (CHCl$_3$, c = 0.670).

EXAMPLE 13

Di-3-pyridoylapomorphine

In accordance with the procedure of Example 2, the aforementioned compound is obtained from 4.55 g. (15 mmol) of apomorphine hydrochloride and 7.06 g. (50 mmol) of nicotinic acid chloride.

Yield: 46.5% of theory; m.p. 131°/133°–135° C.
$[\alpha]_D^{24} = +56.8°$ (CHCl$_3$, c = 0.620).

EXAMPLE 14

Di-4-pyridoylapomorphine

According to the process described in Example 2, the above-mentioned compound is produced from 4.55 g. (15 mmol) of apomorphine hydrochloride and 7.06 g. (50 mmol) of isonicotinic acid chloride.

Yield: 25.1% of theory; m.p. 166°–167° C.
$[\alpha]_D^{23} = +44.4°$ (CHCl$_3$, c = 0.698).

EXAMPLE 15

Di-2-thenoylapomorphine

According to the process of Example 2, one obtains the above-identified compound from 4.55 g. (15 mmol) of apomorphine hydrochloride and 6.6 g. (45 mmol) of thiophene-2-carboxylic acid chloride.

Yield: 49.6% of theory; m.p. 164°–166° C.
$[\alpha]_D^{23} = +55.2°$ (CHCl$_3$, c = 0.650).

EXAMPLE 16

Dicyclopropanoylapomorphine

According to the procedure of Example 2, the aforementioned compound is produced from 4.55 g. (15 mmol) of apomorphine hydrochloride and 6.6 g. (45 mmol) of cyclopropanoyl chloride.

Yield: 81.5% of theory; m.p. 69°–71° C.
$[\alpha]_D^{25} = -64.2°$ (CHCl$_3$, c = 0.620).

EXAMPLE 17

Dicyclobutanoylapomorphine

Analogously to the process of Example 1, the above-mentioned compound is obtained from 4.55 g. (15 mmol) of apomorphine hydrochloride and 5.34 g. (45 mmol) of cyclobutanoyl chloride.

Yield: 66.1% of theory; m.p. 156°–157° C.
$[\alpha]_D^{23} = -70.6°$ (CHCl$_3$, c = 0.48).

EXAMPLE 18

Dicyclopentanoylapomorphine

According to the procedure of Example 1, the afore-described compound is obtained from 4.55 g. (15 mmol) of apomorphine hydrochloride and 5.96 g. (45 mmol) of cyclopentanoyl chloride.

Yield: 53.9% of theory; m.p. 108.5°–110° C.
$[\alpha]_D^{25} = -60.4°$ (CHCl$_3$, c = 0.620).

EXAMPLE 19

Diformylapomorphine 6.08 g. (20 mmol) of apomorphine hydrochloride is dissolved in 300 ml. of formic acid and 10 ml. of acetic anhydride and thereafter heated to 100° C. for 5 hours. Then, the reaction mixture is concentrated under vacuum. The crude product is chromatographed on silica gel with benzene/acetone.

Yield: 53% of theory.
$[\alpha]_D^{23} = -64.5°$ (CHCl$_3$, c = 0.543).

EXAMPLE 20

Diadamantanoylapomorphine

According to the process of Example 2, the above-mentioned compound is obtained from 6.08 g. (20 mmol) of apomorphine hydrochloride and 8.99 g. (45 mmol) of adamantanecarboxylic acid chloride.

Yield: 92.8% of theory; m.p. 233°–235° C.
$[\alpha]_D^{23} = -39.7°$ (CHCl$_3$, $c = 0.718$).

EXAMPLE 21

Dimethoxyacetylapomorphine

According to the procedure of Example 2, the above-identified compound is obtained from 6.08 g. (20 mmol) of apomorphine hydrochloride and 4.89 g. (45 mmol) of methoxyacetyl chloride.

Yield: 66.3% of theory; m.p. 122°–124° C.
$[\alpha]_D^{24.5} = -81.6°$ (CHCl$_3$, $c = 0.622$).

EXAMPLE 22

Di-4-dimethylaminobenzoylapomorphine

In accordance with the procedure of Example 2, the aforementioned compound is produced from 6.08 g. (20 mmol) of apomorphine hydrochloride and 8.25 g. (45 mmol) of 4-dimethylaminobenzoyl chloride.

Yield: 22% of theory; m.p. 220°–223° C.

EXAMPLE 23

Di-n-butyrylapomorphine Hydrogen Tartrate

The di-n-butyrylapomorphine obtained according to Example 2 is dissolved in hot ethanol and mixed with the equivalent amount of tartaric acid in ethanol. After cooling, the colorless crystalline precipitate is vacuum-filtered and recrystallized from ethanol.

Yield: 81% of theory; m.p. 185.5°–186° C.
$[\alpha]_D^{22} = -38.7°$ (CH$_3$OH, $c = 0.452$).

Pharmacological testing was conducted according to a screening program with respect to CNS effectiveness modified according to Irwin, Science, 136:123–128 (1962), as well as with a modified anti-reserpine test. During the screening, the minimum dosages at which certain effects occur which are also displayed by apomorphine hydrochloride are determined as well as the lethal dosage. In the antireserpine test, the minimum dosage which overcomes the catalepsy caused by reserpine treatment is determined in accordance with the method of Zetler, Archives of Experimental Pathology and Pharmacology, 232:442–458 (1958).

The anti-resperpine test is effected as follows:

NMRI [=Naval Medical Research Institute] mice of both sexes weighing 22–25 g. are employed. The animals receive "Altromin" R 10 mixed feed and water ad libitum. For oral administration of test substances, a change is made to feeding with 20% cane sugar solution 24 hours prior to testing.

The test substances are dissolved in saline or suspended in a 0.085% solution of "Myrj 53" (Trademark of Atlas Chemical Industries, Inc. for a series of non-ionic, low-melting point, waxy surface-active agents which are essentially neutral polyoxyethylene derivatives of fat-forming fatty acids) in saline. Lipophilic substances are dissolved in sesame oil or suspended in sesame oil by vacuum distillation from an organic solvent. The test substances are administered to the animals in a descending dosage series (1,600, 800, 400 etc. mg/kg) in an injection volume of 0.2 ml of the appropriate solution or suspension per 20 g. of body weight. Three animals per dosage group are used. A control group receives only the corresponding carrier medium.

For the anti-reserpine test, the animals are pretreated intravenously with 4 mg./kg. of reserpine hydrochloride as a suspension of reserpine hydrochloride in saline using 0.085% "Myrj 53" as a surfactant 24 hours prior to administration of the test substances.

The apomorphine esters tested exhibit a spectrum of apomorphine effects in varyingly pronounced degrees. However, the general duration of action is markedly prolonged; furthermore, the substances, with similar effectiveness, are less toxic than apomorphine (see the Table).

*TABLE:

| | Activity of five Diacylapomorphines and of Apomorphine-HCl in mice | | | | |
|---|---|---|---|---|---|
| | | | RESPONSE | | |
| | | | Anti-Reserpine Test (Abolition of Reserpine-induced Catalepsy) | | Death |
| | | Route of Administration: | i.p. | p.o.  p.o. | i.p. up to |
| SUBSTANCE | Carrier Medium | Time of Testing: | 30' | 30'   60' | 24 hrs. |
| Apomorphine-HCl (Control) | Saline and 0.085 % "Myrj 53" | | 0.20 | 1.56   25 | 100 |
| Diacetylapomorphine | " | | 0.78 | 3.13   6.25 | 200 |
| Diisobutyrylapomorphine | " | | 0.20 | 6.25   6.25 | >800 |
| Apormorphine-HCl (Control) | Sesame Oil | | 0.78 | 0.78   12.5 | 400 |
| Dipropionylapomorphine | " | | 0.78 | 1.56   25 | 800 |
| Dicyclopropanoylapomorphine | " | | 0.05 | 6.25   3.13 | 800 |
| Dibutyrylapomorphine | " | | 0.78 | 0.78   0.78 | 1600 |

*The figures indicate the lowest single doses (mg./kg.) required at different times p.a. to elucidate a full quantal response in abolishing Reserpine-Induced Catalepsy and causing death, resp., using a fixed dosage schedule (1600, 800, 400, 200 etc. mg./kg.).

The effectiveness of these substances in the antireserpine test suggests that they are interesting and valuable agents for the symptomatic treatment of Parkinson's disease. According to Hornykiewicz in Pharmacological Reviews 18:925–964 (1966), it can be assumed that reserpine-induced catalepsy in laboratory animals can be directly compared with the Parkinson syndrome induced by reserpine treatment in humans, as well as with other forms of parkinsonism, since the resulting conditions are in both cases a consequence of a dopamine deficiency of the extrapyramidal system of the CNS. In the screening procedure used, only substances such as L-Dopa and apomorphine are effective, the activity of these substances against parkinsonism symptoms in humans being well-proven as reported by G. C. Cotzias, New. Engl. J. Med 282:31–33 (1970): tricyclic antidepressants, e.g., are ineffective.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A physiologically acceptable apomorphine acyl ester of the formula

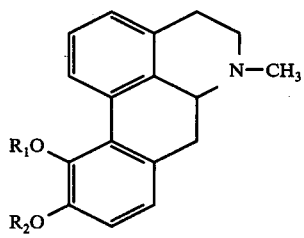

wherein $R_1$ and $R_2$ each are the acyl radical of an alkanoic acid of 3–17 carbon atoms or a cycloalkanoic acid of 3–6 ring members and 4–17 carbon atoms, and its physiologically acceptable acid addition salts.

2. A compound according to claim 1, wherein $R_1 = R_2$ and each are alkanoyl of 3–12 carbon atoms.

3. A compound according to claim 1 selected from the group consisting of diisobutyrylapomorphine, divaleroylapomorphine and dipivaloylapomorphine.

4. The compound of claim 1, di-n-butyrylapomorphine.

5. A compound according to claim 1, wherein $R_1$ and $R_2$ are cycloalkanoyl of 3–6 ring members and 4–12 carbon atoms.

6. A compound according to claim 1 selected from the group consisting of dicyclopropanoylapomorphine, dicyclobutanoylapomorphine, dicyclopentanoylapomorphine and dicyclohexanoylapomorphine.

7. The esters of claim 1 wherein $R_1$ is the acyl radical of a $C_{3-17}$ alkanoic acid and $R_2$ is the acyl radical of a $C_{7-17}$ alkanoic acid or $R_1$ is the acyl radical of a $C_{7-17}$ alkanoic acid and $R_2$ is the acyl radical of a $C_{3-17}$ alkanoic acid.

8. The esters of claim 1 wherein $R_1$ is the acyl radical of a $C_{7-17}$ alkanoic acid and $R_2$ is the acyl radical of butyric, isobutyric, trimethylacetic, α-ethylbutyric, valeric, isovaleric, α-ethylvaleric, 2-methylbutyric, 3-ethylbutyric, hexanoic or diethylacetic acid, or $R_2$ is the acyl radical of a $C_{7-17}$ alkanoic acid and $R_1$ is the acyl radical of butyric, isobutyric, trimethylacetic, α-ethylbutyric, valeric, isovaleric α-ethylvaleric, 2-methylbutyric, 3-ethylbutyric, hexanoic or diethylacetic acid.

9. A compound according to claim 1, wherein $R_1$ and $R_2$ are cycloalkanoyl of 3–6 ring members and 4–17 carbon atoms.

10. A pharmaceutical composition comprising a tremor reducing amount per unit dosage of from 5–500 mg of a physiologically acceptable apomorphine acyl ester of the formula

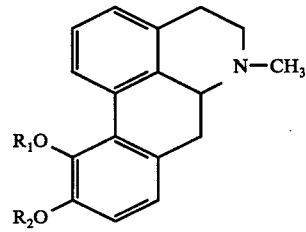

wherein $R_1$ and $R_2$ each are the acyl radical of an alkanoic acid of 3–17 carbon atoms or a cycloalkanoic acid of 3–6 ring members and of 4–17 carbon atoms, or a physiologically acceptable acid addition salt thereof, in admixture with 50–1,000 mg. of a pharmaceutically acceptable carrier.

11. A composition according to claim 10, wherein the apomorphine ester is di-n-butyrylapomorphine.

12. A process for the alleviation of motor disorders in animals which comprises administering systemically a catalepsy-ameliorating effective amount of a physiologically acceptable apomorphine acyl ester of the formula

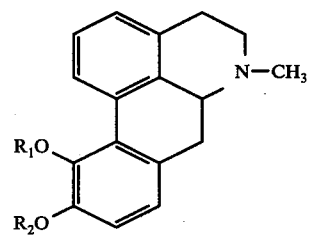

wherein $R_1$ and $R_2$ each are the acyl radical of an alkanoic acid of 3–17 carbon atoms or a cycloalkanoic acid of 3–6 ring members and of 4–17 carbon atoms, or a physiologically acceptable acid addition salt thereof, to a living animal afflicted with dopamine deficiency of the extrapyrimidal system of its central nervous system.

13. A process according to claim 12 wherein the apomorphine ester is di-n-butyrylapomorphine.

* * * * *